United States Patent [19]

Plattner et al.

[11] 4,456,612
[45] Jun. 26, 1984

[54] BENZISOXAZOLE CARBOXYLIC ACIDS

[75] Inventors: Jacob J. Plattner, Libertyville; Anthony K. Fung, Waukegan, both of Ill.

[73] Assignee: Abbott Laboratories, North Chicago, Ill.

[21] Appl. No.: 469,059

[22] Filed: Feb. 23, 1983

Related U.S. Application Data

[63] Continuation-in-part of Ser. No. 300,361, Sep. 8, 1981.

[51] Int. Cl.³ .................. C07D 261/20; C07D 261/00; A61K 31/42
[52] U.S. Cl. .................................. 424/272; 548/242; 548/241; 424/285
[58] Field of Search ................. 424/285, 272; 548/242

[56] References Cited

PUBLICATIONS

Limontschew, et al., "Über Orthobenzotetraphenyldifurfuran", Monatsh 83, (1952) 137–143.
Musante, Carlo, ". . . Furochromone in Quello del Furo–benzo–isossazolo," Gazz. Chem. et al. 88, 910–929, (1958).
Bhawal, et al., "Pesticidal Activity of 1,2 Benzisoxazole . . . ", Marathwada Un. J. Sci., (1978) 17 vol. 21-2.
Hishmat, et al., "Synthesis in Furobenzoxazole . . . ", Z. Naturforsch, B. (1978) 33B(12), 1491–1495.
Limontschew, et al., ". . . Kondensation Von Benzoin und Resorcin," Monatsh 87, (1956), 399–405.

Primary Examiner—Donald G. Daus
Assistant Examiner—A. Hendricks
Attorney, Agent, or Firm—Steven F. Weinstock; Martin L. Katz

[57] ABSTRACT

Described are compounds of the formula

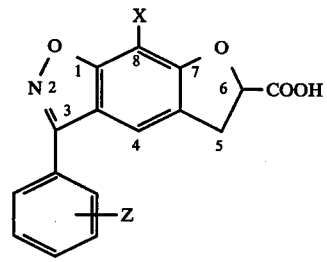

I wherein X is hydrogen, loweralkyl, halo, loweralkoxy or trifluoromethyl, and Z is hydrogen, loweralkyl, halo, hydroxy or alkoxy, or compounds of the formula

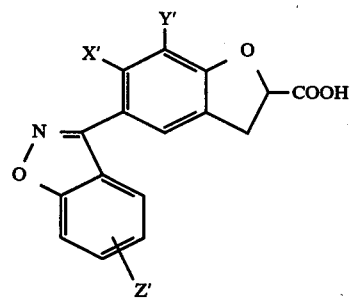

II wherein X' and Y' may be the same or different and are selected from hydrogen, loweralkyl, or halo, and Z' is hydrogen, loweralkyl, halo, hydroxy or loweralkoxy, or pharmaceutically acceptable salts thereof.

The compounds possess diuretic activity.

16 Claims, No Drawings

BENZISOXAZOLE CARBOXYLIC ACIDS

BACKGROUND OF THE INVENTION

This application is a continuation-in-part application of application Ser. No. 300,361 filed Sept. 8, 1981.

The present invention provides compositions for the treatment of hypertension, cardiac failure, edema, and other conditions involving fluid and electrolyte accumulation. A diuretic composition in dosage unit form is described.

SUMMARY OF THE INVENTION

Described are compounds of the formula

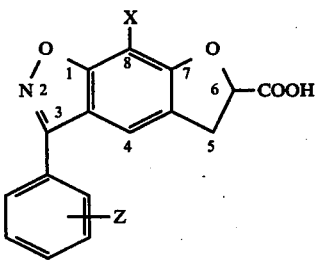

wherein X is hydrogen, loweralkyl, halo, loweralkoxy or trifluoromethyl, and Z is hydrogen, loweralkyl, halo, hydroxy or alkoxy, or compounds of the formula

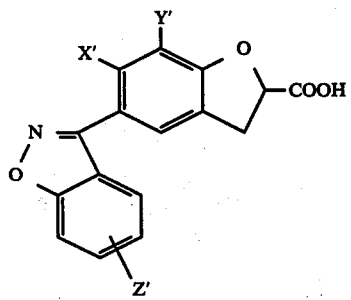

wherein X' and Y' may be the same or different and are selected from hydrogen, loweralkyl, or halo, and Z' is hydrogen, loweralkyl, halo, hydroxy or loweralkoxy, or pharmaceutically acceptable salts thereof.

The term "loweralkyl" and "loweralkoxy" as used herein refer to straight or branched chain alkyl radicals containing from 1 to 6 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic metallic salts such as the sodium, potassium, calcium magnesium or ammonium salt. These can be prepared by reacting the appropriate carboxylic acid with the appropriate metal hydroxide or carbonate.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions. The compounds of this invention can be combined with other compounds having diuretic, antihypertensive or other cardiovascular activity.

A pharmaceutical composition containing the compound can be administered to warm-blooded animals in parenteral or oral dosage forms. For oral administration, amounts of from about 0.1 to 200 mg/kg per day per patient are useful, with the total dose of up to 1 gm. per day being a suitable range for large animals, including humans. A preferred dosage range is 20 to 100 mg. total dosage daily in a single or divided dose. The whole dosage range described increases the total urinary excretion from about 2 to about 10-fold in most animals. From these figures, it is apparent that the new diuretic compounds are particularly effective in increasing urinary excretion in most animals.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

The benzisoxazole carboxylic acids of the invention were prepared according to one of the following reaction schemes:

Scheme 1

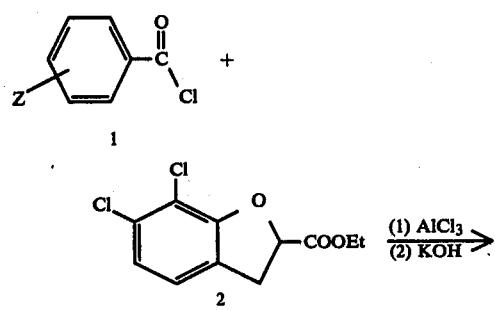

Scheme 1
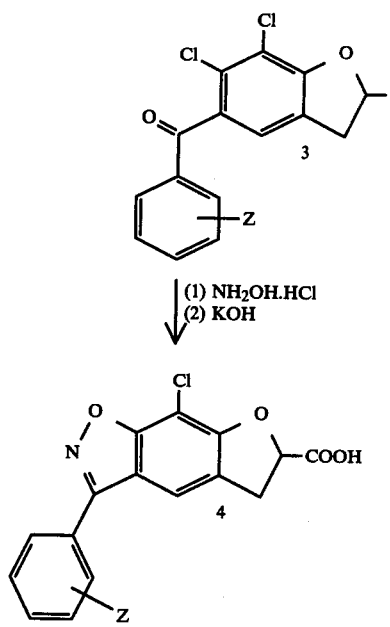
a, Z = H
b, Z = 3-F
c, Z = 4-F
d, Z = 2-Cl
e, Z = 2-Me
f, Z = 4-NO$_2$
g, Z = 4-OH
Scheme 2
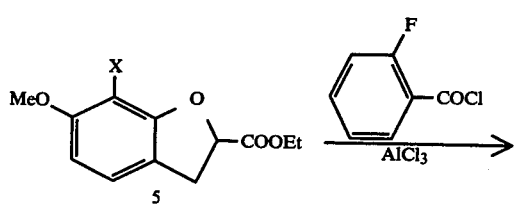
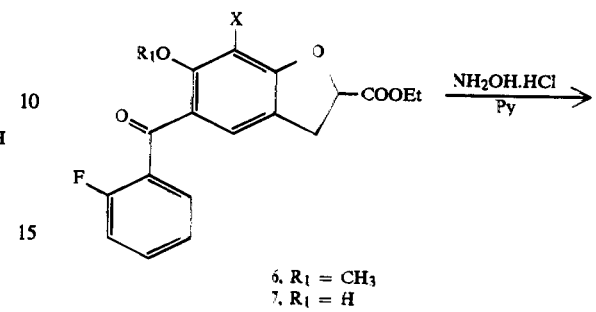
6, R$_1$ = CH$_3$
7, R$_1$ = H
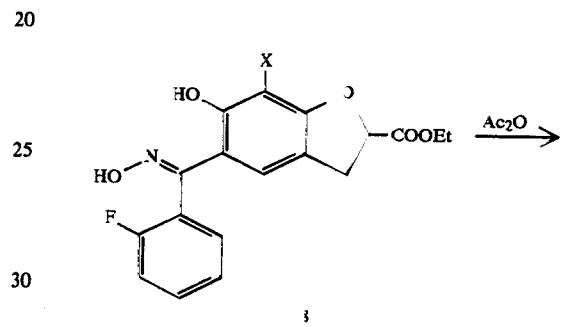
8
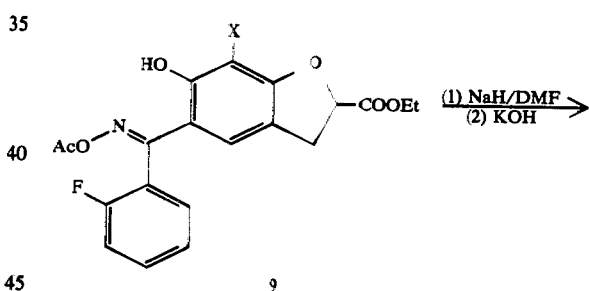
9
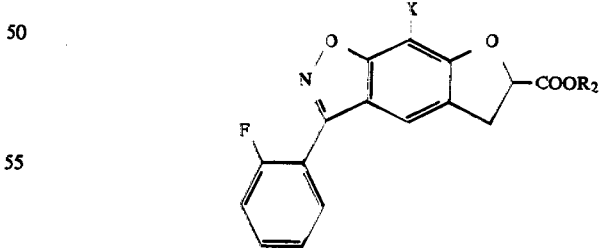
10, R$_2$ = Et
11, R$_2$ = H
For all compounds
h, X = Cl
i, X = Me
j, X = H

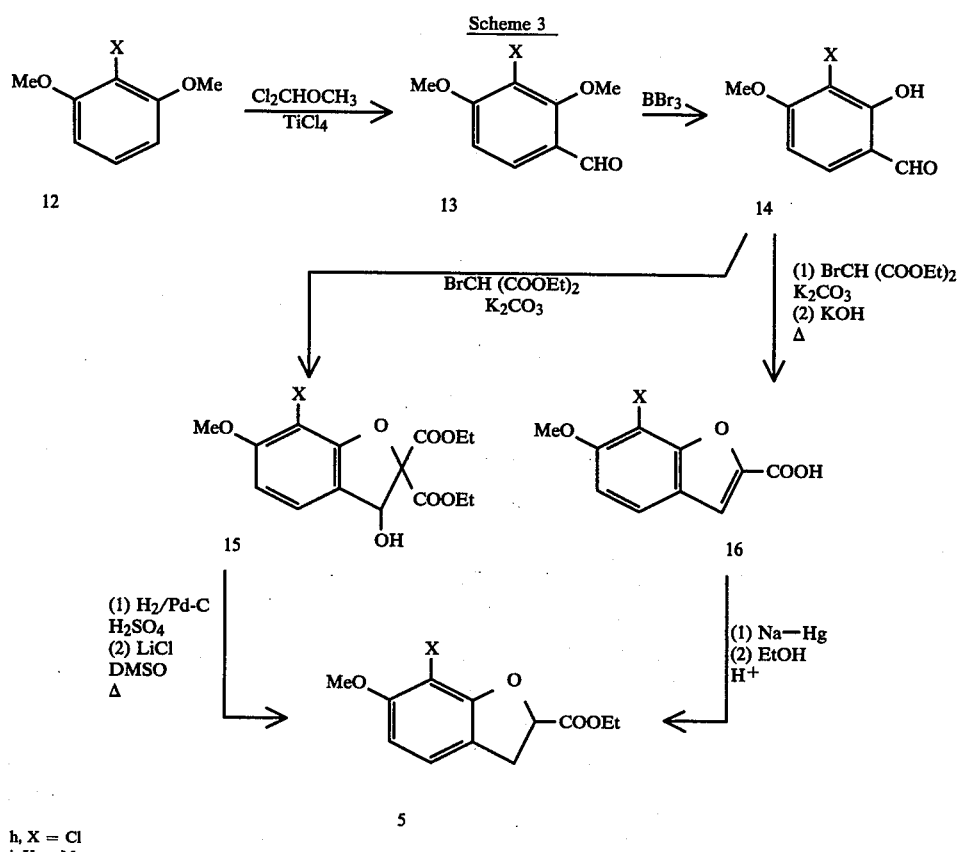
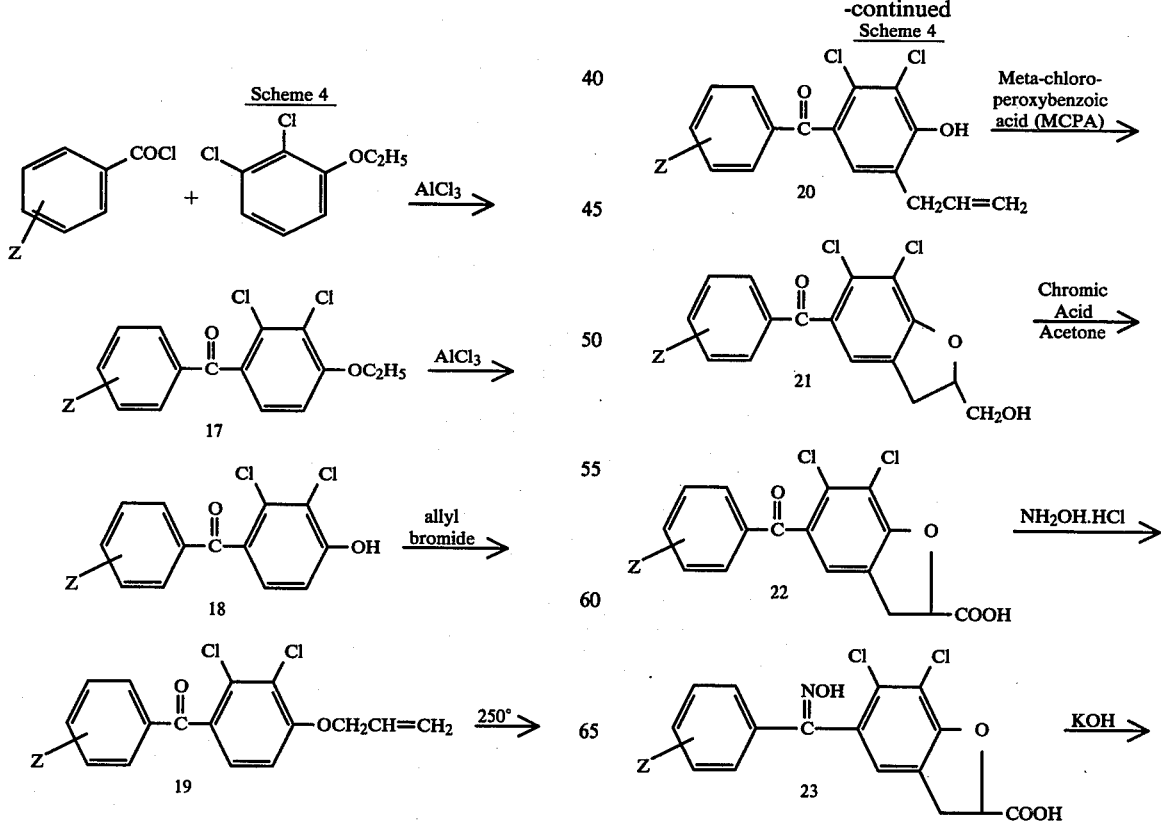
h, X = Cl
i, X = Me
j, X = H

-continued
Scheme 4

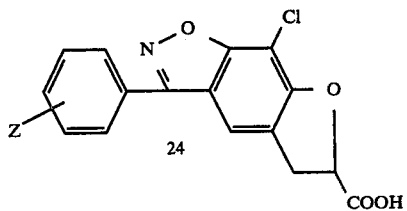

Reaction Scheme 1 was particularly useful for preparing compounds of varying substituents on the pendant phenyl ring. In this process a suitably substituted benzoyl chloride derivative (1) was allowed to react with ethyl 6,7-dichloro-2,3-dihydrobenzofuran-2-carboxylate (2) in a Friedel-Crafts acylation. The resulting benzophenone derivative was hydrolyzed with aqueous base to give the intermediate (3). Treatment of this compound with hydroxylamine hydrochloride in hot pyridine gave the corresponding oxime which was cyclized with base to the desired 8-chloro-3-aryl-5,6-dihydrofuro[3,2-f]-1,2-benzisoxazole-6-carboxylic acid (4).

Reaction Scheme 2 proved to be useful for preparing compounds with different substituents at the 8-position of the dihydrofuro[3,2-f]-1,2-benzisoxazole nucleus. In this process, a dihydrobenzofuran intermediate (5) (prepared in Scheme 3) was subjected to a Friedel-Crafts reaction with o-fluorobenzoyl chloride to give the benzophenone intermediates (6) or (7). Use of mild reaction conditions in this acylation reaction gave the methyl ether (6) whereas more vigorous conditions led directly to the demethylated product (7). Reaction of the benzophenone (7) with hydroxylamine hydrochloride gave the corresponding oxime (8) which was converted to the oxime acetate (9) with acetic anhydride. Cyclization to (10) was achieved by treatment of the oxime acetate intermediate (9) with sodium hydride in N,N-dimethylformamide solution. The final carboxylic acid derivatives (11) were obtained from (10) by a hydrolysis reaction using potassium hydroxide in aqueous ethanol.

The 7-substituted 2,3-dihydrobenzofuran-2-carboxylate intermediates (5) required for use in Reaction Scheme 2 were prepared as indicated in Scheme 3. In this process, a dimethoxybenzene derivative (12) was formylated to (13) using 1,1-dichlorodimethyl ether in the presence of titanium tetrachloride. The methyl ether adjacent to the aldehyde group in (13) was selectively cleaved with boron tribromide giving the salicylaldehyde intermediate (14). From this point, two different pathways to compounds (5) were employed depending on the nature of the X substituent in intermediate (14). In the case of the chloro substituent, the salicylaldehyde (14) was converted to the diester (15) by a reaction with diethyl bromomalonate in the presence of anhydrous potassium carborate. This compound was then converted to (5) by catalytic hydrogenolysis of the hydroxyl function followed by decarbethoxylation with lithium chloride in hot DMSO. The alternative pathway, which was used for the hydrogen and methyl substituents in (14), involved a reaction with diethyl bromomalonate as above, followed by treatment with aqueous potassium hydroxide to give the benzofuran-2-carboxylic acids (16). Sodium-amalgam reduction of (16) followed by esterification then led to compound (5).

The final method of preparing the benzisoxazole carboxylic acids is outlined in Scheme 4.

In this process, the intermediate (17) was prepared by a Friedel-Crafts acylation of the disubstituted phenetole by the appropriately substituted acid chloride. The diaryl ketone can be de-ethylated by any of the usual methods. In the above process, a Lewis acid, aluminum chloride, was used. The anion of the phenol (18) is produced by any base in an appropriate solvent, e.g., $Na_2CO_3$ in acetone or sodium methoxide in methanol, and alkylated with allyl bromide. A thermally induced Claisen rearrangement of the allyl ether (19) gives the phenol (20). Peracid oxidation of (20) produces the dihydrobenzofuran alcohol (21) which is further oxidized to the carboxylic acid (22) with Jones reagent. Formation of the isoxazole ring system is achieved by conversion of the ketone to the corresponding ketoxime (23) and cyclization with potassium hydroxide in ethanol. Separation of the cyclization products as their ethyl esters gives pure samples of each product. Saponification of the ester then leads to the desired product (24).

EXAMPLE 1

5-Benzoyl-6,7-dichloro-2,3-dihydrobenzofuran-2-carboxylic acid (3a)

To a solution of benzoyl chloride (14.71 g., 0.105 mol) and ethyl 6,7-dichloro-2,3-dihydrobenzofuran-2-carboxylate [W. F. Hoffman, et al., J. Med. Chem., 24, 865 (1981)] (13.66 g., 0.0523 mol) in 27 ml. of methylene chloride was added with mechanical agitation anhydrous aluminum chloride (20.92 g., 0.157 mol). The resulting mixture was heated slowly to 90° C. on a hot water bath and held for 1½ hours, during which time it became quite viscous. The mixture was diluted with 100 ml. of 1,2-dichloroethane and decanted into a slurry of 500 ml. ice and 60 ml. concentrated hydrochloric acid. After stirring for 1 hour the slurry was extracted with diethyl ether; and ethereal extract was washed with brine and dried over anhydrous magnesium sulfate. Evaporation yielded a gum which was dissolved in 100 ml. of absolute ethanol and treated with 500 ml. of 2M aqueous potassium hydroxide overnight.

The insoluble potassium salt was collected by filtration and partitioned in a separatory funnel between 4M aqueous hydrochloric acid and diethyl ether. The organic phase was washed with brine, dried over anhydrous magnesium sulfate, decolorized with Darco, filtered and evaporated, affording 17.18 g. of cream powder, m.p. 167°–172° C. On recrystallization from chloroform/n-hexane there was obtained 11.90 g. of (3a), m.p. 188°–190° C. Analysis ($C_{16}H_{10}Cl_2O_4$) C,H.

EXAMPLE 2

6,7-Dichloro-2,3-dihydro-5-(m-fluorobenzoyl)benzofuran-2-carboxylic acid (3b) was obtained from (1b) as in Example 1 in 74.9% yield, m.p. 181.5°–183° C. Analysis ($C_{16}H_9Cl_2FO_4$) C,H.

EXAMPLE 3

6,7-Dichloro-2,3-dihydro-5-(p-fluorobenzoyl)benzofuran-2-carboxylic acid (3c) was obtained from (1c) in the same fashion in 70.4% yield, m.p. 185°–186.5° C. after recrystallization from diethyl ether/n-hexane. Analysis ($C_{16}H_9Cl_2FO_4$) C,H.

EXAMPLE 4

5-(2-Chlorobenzoyl)-6,7-dichloro-2,3-dihydrobenzofuran-2-carboxylic acid (3d) was obtained from (1d) in the same fashion, yielding 70.3%, m.p. 141°–142° C., on recrystallization from ethyl acetate/n-hexane. Analysis ($C_{16}H_9Cl_3O_4$) C,H.

EXAMPLE 5

6,7-Dichloro-2,3-dihydro-5-(o-tolyl)-benzofuran-2-carboxylic acid (3e) resulted in 79.3% yield, m.p. 159°–160.5° C., from the application of the foregoing procedure to (1e). Analysis ($C_{17}H_{12}Cl_2O_4$) C,H.

EXAMPLE 6

6,7-Dichloro-2,3-dihydro-5-(p-nitrobenzoyl)benzofuran-2-carboxylic acid (3f) was obtained in 38.0% yield from (1f), m.p. 249°–250° C., after recrystallization from acetonitrile/1-chlorobutane and trituration in hot distilled water. Analysis ($C_{16}H_9Cl_2NO_6$) C,H,N.

EXAMPLE 7

6,7-Dichloro-2,3-dihydro-5-(p-hydroxybenzoyl)benzofuran-2-carboxylic acid (3g) was obtained from (3f) as follows:

To a stirred suspension of sodium hydride (2.60 g., 0.555 mol., 50% in mineral oil) in N,N-dimethylformamide (40 ml., previously dried over 4 Angstrom molecular sieves) on an ice bath was added acetaldoxime (4.13 g., 0.055 mol.), in portions over 10 minutes. After an additional 10 minutes stirring, a solution of (3f) (6.95 g., 0.0176 mol.) in 30 ml. warm N,N-dimethylformamide was added dropwise, maintaining the temperature below 20° C. The reaction mixture was allowed to reach room temperature and stirred for 6 hours, filtered, and acidified with concentrated hydrochloric acid. The resulting precipitate was collected by filtration, dissolved in ethyl acetate, and washed copiously with distilled water and brine, then dried over anhydrous magnesium sulfate and filtered. Evaporation afforded an oil which was triturated in hexane, yielding 63.0% of solid (3 g.), m.p. 190°–192° C. Analysis ($C_{16}H_{10}Cl_2O_5$) C,H.

EXAMPLE 8

8-Chloro-5,6-dihydro-3-phenylfuro[3,2-f]-1,2-benzisoxazole-6-carboxylic acid (4a)

Hydroxylamine hydrochloride (15.19 g. 0.2186 mol.) and (3a) (10.84 g., 0.0322 mol.) were heated at reflux in 75 ml. of dry pyridine for 5 hours. On cooling, the pyridine was removed on a rotary evaporator and chased with ethanol. The residue, a yellow gum, was taken up in ethyl acetate and washed with dilute aqueous hydrochloric acid and brine, then dried over anhydrous magnesium sulfate and evaporated to a gum containing both E and Z isomers of the oxime. Without further purification, the gum was taken up in 20 ml. of absolute ethanol and treated with 120 ml. of 1M alcoholic potassium hydroxide at reflux on a steam bath for 3 hours then refrigerated at 0°–5° C. for 48 hours. The resulting precipitate was collected by filtration, washed with hexane, dried, and dissolved in 300 ml. warm distilled water. Acidification to pH 2.0 by addition of 4.0M aqueous hydrochloric acid gave a gelatinous precipitate which was extracted into ethyl acetate, dried with anhydrous magnesium sulfate, decolorized with Darco, and evaporated. Recrystallization from ethyl acetate with hexane afforded the furobenzisoxazole (4a) in 32.3% yield, m.p. 214°–215° C. Analysis ($C_{16}H_{10}ClNO_4$) C,H,N,Cl.

EXAMPLE 9

8-Chloro-5,6-dihydro-3-(m-fluorophenyl)furo[3,2-f]-1,2-benzisoxazole-6-carboxylic acid (4b) was obtained in 28.4% yield, m.p. 182.5°–183.5° C., from (3b) in an analogous manner, and recrystallized from chloroform with petroleum ether. Analysis ($C_{16}H_9ClFNO_4$) C,H,N.

EXAMPLE 10

8-Chloro-5,6-dihydro-3-(p-fluorophenyl)furo[3,2-f]-1,2-benzisoxazole-6-carboxylic acid (4c) was prepared from (3c) by a similar method. Recrystallization from chloroform/petroleum ether gave a 26.6% yield, m.p. 225°–226° C. Analysis ($C_{16}H_9ClFNO_4$) C,H,N.

EXAMPLE 11

8-Chloro-3-(o-chlorophenyl)-5,6-dihydrofuro[3,2-f]-1,2-benzisoxazole-6-carboxylic acid (4d) was prepared from (3d) using the procedure above; the product contained a significant impurity, presumably the countercyclized 5-(3-benzisoxazolyl)-6,7-dichloro-2,3-dihydrobenzofuran-2-carboxylic acid. The mixture was dissolved in 200 ml. absolute ethanol and treated with 0.5 ml. concentrated sulfuric acid overnight. The solution was then evaporated to dryness, redissolved in ethyl acetate, washed with brine, dried over anhydrous magnesium sulfate, and re-evaporated. Chromatography of the ester on silica gel with chloroform and n-hexane in a 3:1 ratio gave a solid, m.p. 136° C., which was determined by detailed mass spectral analysis to be the desired isomer. Hydrolysis at 60° C. in 25 ml. absolute ethanol and 200 ml. aqueous 1M sodium hydroxide for 20 minutes furnished a white precipitate which was distributed between ethyl acetate and 4.0M aqueous hydrochloric acid, washed with brine, dried over anhydrous magnesium sulfate, and evaporated. Recrystallization from ethyl acetate with n-hexane gave (4d), m.p. 224°–225° C., in 8.1% yield. Analysis ($C_{16}H_9Cl_2NO_4$) C,H,N,Cl.

EXAMPLE 12

8-Chloro-5,6-dihydro-3-(o-tolyl)furo[3,2-f]-1,2-benzisoxazole-6-carboxylic acid (4e) was prepared in a fashion analogous to (4a) from (3e). A tenacious impurity resulted in the need for esterification, chromatography, and hydrolysis as with (4d). Trituration in n-hexane produced (4e) in 9.4% yield, m.p. 179°–181° C. Analysis ($C_{17}H_{12}ClNO_4$) C,H,N.

EXAMPLE 13

Potassium 8-Chloro-5,6-dihydro-3-(p-hydroxyphenyl)furo[3,2-f]-1,2-benzisoxazole-6-carboxylate (4g) was prepared from (3g) in the same manner as Example 8. Acidification of an aqueous solution of the dipotassium salt afforded the insoluble monopotassium salt as a precipitate which was triturated in warm distilled water and dried to furnish (4g), m.p. 215°–217° C., in 47.0% yield. Analysis ($C_{16}H_9ClKNO_5$) C,H,N.

EXAMPLE 14

Ethyl 7-Chloro-2,3-dihydro-5-(o-fluorobenzoyl)-6-hydroxybenzofuran-2-carboxylate (7h)

A solution of (5h) (7.79 g., 0.0304 mol.) and o-fluorobenzoyl chloride (7.25 ml., 0.0607 mol.) in 80 ml. of 1,2-dichloroethane was stirred on an ice-brine bath and treated with anhydrous aluminum chloride (16.17 g., 0.1215 mol.) in small portions, keeping the temperature below 5° C. After 45 minutes cooling, the mixture was removed and the reaction mixture was allowed to stir at room temperature for 3 hours. Decantation into iced dilute aqueous hydrochloric acid followed by gentle warming produced a pale yellow oil which was extracted into ethyl acetate. The extract was washed with brine, dried over anhydrous magnesium sulfate, decolorized with Darco and evaporated, yielding 69.2% of (7h), m.p. 119°–119.5° C., on recrystallization from ethyl acetate/n-hexane. Analysis ($C_{18}H_{14}ClFO_5$) C,H.

EXAMPLE 15

Ethyl 2,3-Dihydro-5-(o-fluorobenzoyl)-6-hydroxy-7-methyl benzofuran-2-carboxylate (7i)

A solution of (5i) (2.7 g., 0.011 mole) and o-fluorobenzoyl chloride (2.73 ml., 0.022 mole) in 30 ml. of 1,2-dichloroethane was stirred at 0°–5° C. and treated with anhydrous aluminum chloride (4.57 g., 0.05 mole) in small portions. After 10 minutes, the reaction mixture was poured onto ice and then extracted with methylene chloride. The organic layer was washed with brine solution, dried over magnesium sulfate and evaporated to give a 68% yield of ethyl 2,3-dichloro-5-(o-fluorobenzoyl)-6-methoxy-7-methylbenzofuran-2-carboxylate, m.p. 101.5°–102.5° C. A solution of this compound (2.0 g., 0.0056 mole) in 20 ml. of methylene chloride was cooled to 0° C. and treated by dropwise addition with 6.14 ml. (0.006 mole) of 1M boron tribromide/methylene chloride. After 15 minutes, the reaction was poured into ice water and the resulting mixture extracted with methylene chloride. The organic layer was dried over magnesium sulfate and evaporated to give a 93% yield of (7i) after recrystallization from ethanol, m.p. 103.5°–105.5° C. Analysis ($C_{19}H_{17}FO_5$) C,H.

EXAMPLE 16

Ethyl 2,3-dihydro-5-(o-fluorobenzoyl)-6-hydroxybenzofuran-2-carboxylate (7j) was obtained from (5j) in 62% yield using the procedure of Example 15, m.p. 120°–121° C. Analysis ($C_{18}H_{15}FO_5$) C,H.

EXAMPLE 17

Ethyl (E)-7-chloro-2,3-dihydro-5-(o-fluorobenzoyl)-6-hydroxybenzofuran-2-carboxylate Oxime (8h)

A solution of (7h) (6.69 g., 0.01834 mol) in 100 ml. of methylene chloride was cooled on an acetonitrile/dry ice bath and treated dropwise with 55 ml. of 1M boron tribromide/methylene chloride solution. The solution was stirred at room temperature overnight. The resulting orange mixture was decanted into dilute iced aqueous hydrochloric acid and warmed gently to room temperature, stirred for 2 hours, and extracted into ethyl acetate. The organic phase was washed with brine, dried over anhydrous magnesium sulfate, and decolorized with Darco. Evaporation and recrystallization from ethyl acetate/n-hexane gave the free acid in 53.8% yield, m.p. 209.5°–212.5° C. Analysis ($C_{16}H_{11}ClFNO_5$) C,H.

A portion of this material (3.13 g., 0.00093 mol) was dissolved in 100 ml. of pyridine to which hydroxylamine hydrochloride (4.25 g., 0.0651 mol.) was added. After refluxing for 6 hours, the pyridine was removed on a rotary evaporator and chased with absolute ethanol. The resulting gum was partitioned between distilled water and ethyl acetate, and the organic phase collected. This solution was washed copiously with dilute aqueous hydrochloric acid and with brine, then dried over anhydrous magnesium sulfate and decolorized with Darco. Evaporation and trituration with ethyl acetate/n-hexane afforded the ketoxime in quantitative yield, m.p. 195°–197° C. Analysis ($C_{16}H_{11}ClFNO_5$) C,H,N.

A sample of this material was esterified in 25 ml. of absolute ethanol with 10 drops of concentrated sulfuric acid for 3.5 hours, then evaporated and redissolved in ethyl acetate. The solution was washed with brine, iced aqueous sodium bicarbonate, and additional brine, dried over anhydrous magnesium sulfate, and evaporated to an oil. Recrystallization from ethyl acetate/n-hexane yielded 74.0% of (8h), m.p. 171°–172° C. Analysis ($C_{18}H_{14}ClFNO_5$) C,H,N.

EXAMPLE 18

Ethyl (E)-2,3-dihydro-5-(o-fluorobenzoyl)-6-hydroxy-7-methylbenzofuran-2-carboxylate Oxime (8i)

A mixture of (7i) (1.6 g., 4.65 mmole) and hydroxylamine hydrochloride (1.55 g., 22.3 mmole) was heated at reflux in 7 ml. of pyridine for 4 hours. The solvent was evaporated and the residue was partitioned between ethyl acetate and 5% HCl. From the organic phase was obtained 0.34 g. (20%) of (8i) after chromatographic purification on silica gel, m.p. 70°–71° C. Analysis ($C_{19}H_{18}FNO_5$) C,H,N.

EXAMPLE 19

Ethyl (E)-2,3-dihydro-5-(o-fluorobenzoyl)-6-hydroxybenzofuran-2-carboxylate Oxime (8j)

Using the procedure described in Example 18, (8j) was obtained in 24% yield from (7j), m.p. 179°–181° C. Analysis ($C_{18}H_{16}FNO_5$) C,H,N.

EXAMPLE 20

Ethyl (E)-7-chloro-2,3-dihydro-5-(o-fluorobenzoyl)-6-hydroxybenzofuran-2-carboxylate O-Acetyl oxime (9h)

To acetic anhydride (8 ml.) was added (8h) (400 mg., 1.06 mmole). After stirring for 1 hour at 90° C. the mixture was left to stand at room temperature for 18 hours, then evaporated to dryness under high vacuum. The product, an oil, was triturated in absolute ethanol, giving crystalline (9h), m.p. 111°–112° C. in 58.4% yield. Analysis ($C_{20}H_{17}ClFNO_6$) C,H,N.

EXAMPLE 21

Ethyl (E)-2,3-dihydro-5-(o-fluorobenzoyl)-6-hydroxy-7-methylbenzofuran-2-carboxylate O-Acetyl oxime (9i)

Using the procedure described in Example 20, (9i) was obtained in 60% yield from (8i).

EXAMPLE 22

Ethyl
(E)-2,3-dihydro-5-(o-fluorobenzoyl)-6-hydroxyfuran-2-carboxylate O-Acetyl oxime (9j)

Using the procedure described above in Example 20, (9j) was prepared in 55% yield from (8j).

EXAMPLE 23

Ethyl
8-Chloro-5,6-dihydro-3-(o-fluorophenyl)furo[3,2-f]-1,2-benzisoxazole-6-carboxylate (10h)

The acetate (9h) (400 mg., 0.001 mol) was dissolved in 5 ml. of dry N,N-dimethylformamide and stirred on an ice bath under inert atmosphere. A 45 mg. portion of 50% sodium hydride/mineral oil was introduced and cooling removed. After (4h) the mixture was decanted into iced brine and the crude (10h) collected by filtration.

This product was dissolved in ethyl acetate, washed with brine and aqueous sodium bicarbonate solutions, dried over anhydrous magnesium sulfate and evaporated. Recrystallization from ethanol/water gave 37.9% of (10h), m.p. 134°–136° C. Analysis ($C_{18}H_{13}ClFNO_4$) C,H,N.

EXAMPLE 24

Ethyl
5,6-dihydro-3-(o-fluorophenyl)-8-methylfuro[3,2-f]-1,2-benzisoxazole-6-carboxylate (10i)

Employing the procedure described above in Example 23, (10i) was prepared in 42% yield from (9i), m.p. 124°–125° C. Analysis ($C_{19}H_{16}FNO_4$) C,H,N.

EXAMPLE 25

Ethyl
5,6-dihydro-3-(o-fluorophenyl)furo[3,2-f]-1,2-benzisoxazole-6-carboxylate (10j)

Using the procedure described in Example 23, (10j) was prepared in 53% yield from (9j), m.p. 115°–116° C. Analysis ($C_{18}H_{14}FNO_4$) C,H,N.

EXAMPLE 26

8-Chloro-3-(o-fluorophenyl)-5,6-dihydrofuro[3,2-f]-1,2-benzisoxazole-6-carboxylic acid (11h)

To a solution of (10h) (1 g., 2.76 mmole) in 10 ml. of warm methanol was added a solution of potassium hydroxide (0.31 g., 5.52 mmole) in 1 ml. of water. After 1 hour, the reaction mixture was partially evaporated, diluted with water and warmed to dissolve the resulting potassium salt. Acidification with 2N hydrochloric acid gave a white precipitate which was filtered and dried. There was obtained 0.85 g. (92%) of (11h), m.p. 197.5°–199° C. Analysis ($C_{16}H_9ClFNO_4$) C,H,N.

EXAMPLE 27

3-(o-Fluorophenyl)-5,6-dihydro-8-methylfuro[3,2-f]-1,2-benzisoxazole-6-carboxylic acid (11i)

Using the procedure described in Example 26, (11i) was prepared in 89% yield from (10i), m.p. 188°–189° C. Analysis ($C_{17}H_{12}FNO_4$) C,H,N.

EXAMPLE 28

3-(o-Fluorophenyl)-5,6-dihydrofuro[3,2-f]-1,2-benzisoxazole-6-carboxylic acid (11j)

Employing the procedure described in Example 26, (11j) was prepared in 90% yield from (10j), m.p. 194°–196° C. Analysis ($C_{16}H_{10}FNO_4$) C,H,N.

EXAMPLE 29

3-Chloro-2,4-dimethoxybenzaldehyde (13h)

To a solution of 10.0 g. (0.058 mol) of 2-chlororesorcinol dimethyl ether [G. N. Shutske, et al., J. Med. Chem., 25, 36(1982)] in 75 ml. of $CH_2Cl_2$ at −40° C. under $N_2$ was added dropwise 12.7 ml. (0.116 mol) of $TiCl_4$. This was followed by dropwise addition of 6.7 g. (0.58 mol) of dichloromethyl methyl ether at −20° C. The mixture was stirred for 1 hour at 0° C. and then was allowed to warm to room temperature. The reaction mixture was poured into 100 ml. of 1:1 HCl/ice water and then was extracted with $CH_2Cl_2$. The organic solution was washed with dilute $NaHCO_3$ and then with aqueous NaCl. After drying over $Na_2SO_4$, the $CH_2Cl_2$ was evaporated to provide 9.2 g. of (13h), m.p. 109°–111° C. Analysis ($C_9H_9ClO_3$) C,H.

EXAMPLE 30

3-Methyl-2,4-dimethoxybenzaldehyde (13i)

Using the procedure described above in Example 29, (13i) was prepared in 73% yield from 2,6-dimethoxytoluene, m.p. 51°–52° C. Analysis ($C_{10}H_{12}O_3$) C,H.

EXAMPLE 31

3-Chloro-2-hydroxy-4-methoxybenzaldehyde (14h)

To a solution of 72.0 g. (0.359 mol) of (13h) in 450 ml. of $CH_2Cl_2$ at −50° C. under $N_2$ was added dropwise 90.0 g. (0.359 mol) of $BBr_3$. After the addition was complete, the reaction mixture was warmed to 0° C. and stirred for 1 hour. The reaction mixture was then poured into 500 ml. of ice-water and extracted with EtOAc. The organic solution was washed with aqueous NaCl and dried over $Na_2SO_4$. Evaporation of the EtOAc gave a residue that was rapidly passed through a silica gel column eluting with an $EtOAc/CH_2Cl_2$ mixture. This afforded 49.5 g. of (14h), m.p. 114°–117° C. Analysis ($C_8H_7ClO_3$) C,H.

EXAMPLE 32

2-Hydroxy-4-methoxy-3-methylbenzaldehyde (14i)

Using the procedure described in Example 31, (14i) was prepared from (13i) in 75% yield.

EXAMPLE 33

Diethyl
7-chloro-2,3-dihydro-3-hydroxy-6-methoxybenzofuran-2,2-dicarboxylate (15h)

To a solution of (14h) (69.91 g., 0.375 mol) and diethyl bromomalonate (79.9 ml., 0.468 mol) in 2-butanone (400 ml.) was added freshly powdered anhydrous potassium carbonate (51.78 g.). The suspension was stirred vigorously and heated at reflux for 4.5 hours, then filtered and evaporated to dryness. The oil obtained was redissolved in carbon tetrachloride and filtered, then evaporated and recrystallized from chloroform with hexane to yield 79.6% of (15h), m.p. 115.5°–117° C. Analysis ($C_{15}H_{17}ClO_7$) C,H.

EXAMPLE 34

6-Methoxy-7-methylbenzofuran-2-carboxylic acid (16i)

A mixture of 2-hydroxy-4-methoxy-3-methylbenzaldehyde (68 g., 0.41 mole), diethyl bromomalonate (102.8 g., 0.43 mole) and anhydrous potassium carbonate (55 g., 0.4 mole) in 250 ml. of methyl ethyl ketone was heated at reflux for 4 hours. After filtering, the filtrate was partly evaporated and the residue distributed between methylene chloride and aqueous sodium chloride solution. The organic layer was dried and evaporated to a residue. This material was dissolved in 85 ml. of absolute ethanol and treated all at once with a hot solution of 47.5 g. of potassium hydroxide in 500 ml. of ethanol. The potassium carboxylate which precipitated was filtered and then dissolved in a minimum amount of water. Acidification with 6N HCl gave, after cooling and filtration, a 55% yield of the desired product (16i), m.p. 237°–239° C. Analysis ($C_{11}H_{10}O_4$) C,H.

EXAMPLE 35

Ethyl 7-Chloro-2,3-dihydro-6-methoxybenzofuran-2-carboxylate (5h)

A solution of (15h) (2.67 g., 0.008 mol) and 3 drops of concentrated sulfuric acid in 100 ml. of glacial acetic acid was treated with 0.3 g. of 20% palladium on carbon in a Parr apparatus under 3 atmospheres of hydrogen for 2 hours at room temperature. The solvent was evaporated under reduced pressure and the residue was dissolved in chloroform. This solution was washed with aqueous sodium bicarbonate and brine solutions, dried over anhydrous sodium sulfate, and evaporated. There resulted an 82.5% yield of diethyl 7-chloro-2,3-dihydro-6-methoxybenzofuran-2,2-dicarboxylate, m.p. 97°–99° C. Analysis ($C_{15}H_{17}ClO_6$) C,H.

The above intermediate (16.79 g., 0.0509 mol), distilled water (1.0 ml., 0.0555 mol.), dry lithium chloride (4.36 g., 0.1018 mol) and dimethylsulfoxide (150 ml., previously dried over 5 Angstrom molecular sieves) were combined and heated at reflux for 2 hours, then allowed to cool to 90° C. Most of the dimethylsulfoxide was removed by vacuum distillation, and the residue decanted into excess brine solution. The brine was acidified with concentrated hydrochloric acid and extracted several times with ethyl acetate. The combined washes were in turn washed copiously with fresh brine, and then evaporated. The residue obtained was dissolved in 300 ml. of dry EtOH containing 1 ml. of $H_2SO_4$ and stirred overnight at room temperature. The ethanol was evaporated and replaced with ethyl acetate and this solution was washed with aqueous sodium bicarbonate and brine solutions. Drying over anhydrous magnesium sulfate, decolorization with Darco, and evaporation followed by recrystallization from ethanol/water afforded a 69.0% yield of (5h), m.p. 108.5°–110° C. Analysis ($C_{12}H_{13}ClO_4$) C,H.

EXAMPLE 36

Ethyl 2,3-dihydro-6-methoxy-7-methylbenzofuran-2-carboxylate (5i)

To a solution of (16i) (29 g., 0.14 mole) dissolved in aqueous sodium hydroxide (15 g. NaOH in 750 ml. of water) was added 550 g. of 5% sodium amalgam portionwise over a period of 30 minutes. The mixture was stirred for 5 hours and then decanted from the mercury and filtered through Celite. The filtrate was acidified with hydrochloric acid and cooled in an ice bath. There was obtained 26 g. of crude acid after filtering. Recrystallization from methylene chloride/hexane gave pure 2,3-dihydro-6-methoxy-7-methylbenzofuran-2-carboxylic acid, m.p. 142°–143° C. Esterification of this material by the procedure described in Example 35 gave (5i) as an oil. Analysis ($C_{13}H_{16}O_4$) C,H.

EXAMPLE 37

Ethyl 2,3-dihydro-6-methoxybenzofuran-2-carboxylate (5j)

This compound was prepared in 53% overall yield from 6-methoxybenzofuran-2-carboxylic acid [S. Tanaka, J. Am. Chem. Soc., 73, 872 (1951)] using the procedure of Example 36.

EXAMPLE 38

2,3-Dichloro-4-(2-fluorobenzoyl)phenetole

A mixture of 2,3-dichlorophenetole (57.3 g., 0.3 mole), 2-fluorobenzoyl chloride (47.8 g., 0.3 mole) and methylene chloride (300 ml.) at 5° C. was stirred vigorously and treated with finely powdered aluminum chloride (42.6 g., 0.32 ml.). The reaction mixture was slowly warmed to room temperature and then stirred overnight. The reaction mixture was decomposed with ice/concentrated hydrochloric acid (50 ml.) and the aqueous solution was extracted twice with methylene chloride. The combined organic extracts were washed with aqueous sodium bicarbonate solution and finally with aqueous sodium chloride solution. The methylene chloride solution was dried over $MgSO_4$ and filtered. The solvent was removed in vacuo and the residue on triturating with methanol gave the product 55 g., m.p. 94°–95° C. This material was used in the next step without additional purification.

EXAMPLE 39

2,3-Dichloro-4-(2-fluorobenzoyl) Phenol

A solution of 54 g. (0.172 mole) of the compound from Example 38 in 325 ml. of methylene chloride was treated slowly with 46 g. (0.345 mole) of $AlCl_3$ and the resulting mixture thus obtained was refluxed for 3 hours. The reaction mixture was cooled to room temperature and decomposed with ice water. The aqueous phase was extracted with methylene chloride and the combined organic solution ie extracted with a cold solution of 5% potassium hydroxide in water. The alkaline solution was acidified with concentrated hydrochloric acid and the resulting precipitate was dissolved in ethyl acetate, dried ($MgSO_4$) and evaporated. The residue was triturated with petroleum ether and the product was collected by filtration to give 46 g., m.p. 143°–144° C.

EXAMPLE 40

2,3-Dichloro-6-propenyl-4-(2-fluorobenzoyl)phenol

A mixture of 2,3-dichloro-4-(2-fluorobenzoyl)phenol (98 g., 0.343 mole), $K_2CO_3$ (94 g., 0.68 mole), allyl bromide (37 ml., 0.425 ml.) and 750 ml. of 2-butanone was heated at reflux for 4 hours. After cooling the 2-butanone was partially evaporated and the residue distributed between methylene chloride and aqueous NaCl. The organic layer was dried and evaporated to give 105 g. of the intermediate propenyl ether as a liquid. This material was dissolved in an equal volume of diphenyl ether and heated at 250° for 3.5 hours. The cooled reaction mixture was diluted with hexane and washed several times with 1N aqueous KOH. The combined aqueous washes were acidified with 6N HCl and the resulting mixture extracted with methylene chloride. The methylene chloride solution was dried (MgSO$_4$) and evaporated to a residue. Trituration with hexane gave 73 g. of solid product, m.p. 83°–84° C.

EXAMPLE 41

6,7-Dichloro-2,3-dihydro-5-(2-fluorobenzoyl)-2-hydroxymethylbenzofuran

A mixture of 2,3-dichloro-6-propenyl-4-(2-fluorobenzoyl)phenol (62.5 g., 0.192 mole) and m-chloroperoxybenzoic acid (47.6 g., 0.22 mole) in 550 ml. of methylene chloride was stirred at room temperature for 24 hours. The precipitated m-chlorobenzoic acid was removed by filtration and the filtrate was washed successively with 5% aqueous sodium sulfite and 10% aqueous sodium bicarbonate. The methylene chloride was kept at room temperature for 4 days and then washed with 0.5N NaOH solution. After drying over MgSO$_4$, the solvent was evaporated to give 45 g. of solid product, m.p. 148°–150° C.

EXAMPLE 42

6,7-Dichloro-2,3-dihydro-5-(2-fluorobenzoyl)benzofuran-2-carboxylic acid

Jones reagent [J. Chem. Soc., 2555 (1953)] (84 ml.) was added dropwise to a stirred, cooled solution of 6,7-dichloro-2,3-dihydro-5-(2-fluorobenzoyl)-2-hydroxymethylbenzofuran (43 g., 0.126 mole) in acetone (700 ml.) at such a rate that the internal temperature did not exceed 25° C. The resultant mixture was stirred for 18 hours at 25° C. The insoluble chromium salts were separated by decantation and washed with acetone. The washings were combined with the filtrate, and the resultant solution was concentrated to 1/5 the original volume and then poured into H$_2$O. This mixture was extracted with methylene chloride and the organic extract was washed several times with aqueous NaCl. The methylene chloride solution was then extracted with 0.5N KOH. Upon standing the aqueous extract deposited the potassium carboxylate salt as a crystalline solid. The solid was dissolved in warm water, acidified with 6N HCl and the resulting solution extracted with ethyl acetate. Drying and evaporation furnished 38 g. of carboxylic acid, m.p. 180°–181° C. This material was used without additional purification for the next step.

EXAMPLE 43

8-Chloro-3-(2-fluorophenyl)-5,6-dihydrofuro[3,2-f]-1,2-benzisoxazole-6-carboxylic acid A mixture of 6,7-dichloro-2,3-dihydro-5-(2-fluorobenzoyl)benzofuran-2-carboxylic acid (15 g.) hydroxylamine hydrochloride (20 g.) and pyridine (80 ml.) was heated at reflux for 5 hours. The pyridine was evaporated under reduced pressure and the residue poured slowly into cold, 5% HCl. The resulting solid was filtered and dried to give 12 g. of the corresponding oxime. The oxime was dissolved in 100 ml. of absolute ethanol and mixed with a solution of 9.4 g. of potassium hydroxide in 150 ml. of ethanol. After refluxing for 2 hours, the solution was allowed to cool and the precipitated potassium carboxylate salt was filtered. This salt was converted to the free acid as described in Example 42 and then esterified by stirring overnight in 150 ml. of ethanol containing 0.5 ml. of concentrated H$_2$SO$_4$. Partial evaporation of the ethanol was followed by distribution of the residue between methylene chloride and saturated aqueous HCl. The organic phase was dried and evaporated to give a mixture of ethyl esters. The mixture was subjected to preparative high pressure liquid chromatography to afford pure samples of ethyl 8-chloro-3-(2-fluorophenyl)-5,6-dihydrofuro[3,2-f]-1,2-benzizisoxazole-6-carboxylate, m.p. 135°–136° C. and ethyl 5-(1,2-benzisoxazole-3-yl)-6,7-dichloro-2,3-dihydrobenzofuran-2-carboxylate, m.p. 114°–116° C. The corresponding carboxylic acids were obtained by hydrolysis with potassium hydroxide. Thus, a 1 g. sample of each ester was dissolved in 25 ml. of 80% aqueous methanol containing 2 molar equivalents of KOH. After 2 hours at room temperature, the methaol was partially evaporated and the residue diluted with water. Acidification with hydrochloric acid furnished the acids: 8-chloro-3-(2-fluorophenyl)-5,6-dihydrofuro[3,2-f]-1,2-benzisoxazole-6-carboxylic acid, m.p. 197.5°–199° C.

Analysis Calcd. for C$_{16}$H$_9$ClFNO$_4$: C, 57.59; H, 2.72; N, 4.20 Found: C, 58.26; H, 2.61; N, 4.24.

5-(1,2-benzisoxazole-3-yl)-6,7-dichloro-2,3-dihydrobenzofuran-2-carboxylic acid, m.p. 197°–200° C.

Analysis Calcd. for C$_{16}$H$_9$CL$_2$NO$_4$: C, 54.85; H, 2.57; N, 4.00 Found: C, 54.58; H, 2.41; N, 4.23.

The preferred compounds of the invention are 8-chloro-5,6-dihydro-3-(o-tolyl)-furo[3,2-f]-1,2-benzisoxazole-6-carboxylic acid; 8-chloro-5,6-dihydro-3-(p-fluorophenyl)-furo[3,2-f]-1,2-benzisoxazole-6-carboxylic acid; 8-chloro-3-(o-fluorophenyl)-5,6-dihydrofuro[3,2-f]-1,2-benzisoxazole-6-carboxylic acid; and 3-(o-fluorophenyl)-5,6-dihydro-8-methylfuro[3,2-f]-1,2-benzisoxazole-6-carboxylic acid; with the compound 8-chloro-3-(o-fluorophenyl)-5,6-dihydrofuro[3,2-f]-1,2-benzisoxazole-6-carboxylic acid being the most preferred.

Compounds of the invention were studied in nonfluid-loaded female beagle dogs for evaluation of the effects on urine volume, plasma levels and urinary excretion of sodium, potassium and glucose.

The dogs were starved for 18–20 hours prior to dosing but were allowed free access to water. Food and water were not allowed after dosing until the completion of the experiment. The compound were administered by gavage. The dose treated was 30 mg./kg. Urine samples from the catherized bladder were collected at -½–0, 0–1, 1–2, 2–4, and 4–6 hours relative to the time of dosing.

The compound of Formula I in which X is chloro and Z is 2-fluoro, was found to produce a mean cumulative urine volume in milliliters per kilogram of 59.06 in six hours, after administration in contrast to the control animal which excreted a mean cumulative urine volume of 2.94 mg./kg. in six hours. The cumulative sodium excretion in six hours after administration was found to be 7.54 milliequivalents per kilogram whereas the control animal excreted 0.17 meq/kg. in the same time period.

The compound of Formula II wherein Y is chloro and Z is hydrogen produced a mean cumulative urine volume of 46.50 ml./kg. in contrast to 2.94 for the control animal and a cumulative sodium excretion of 6.05 meq/kg. in contrast to 0.17 meq/kg. for the control animal, all in six hours after administration of the drug.

Diuretic screening of the compounds of Formula I of this invention was conducted in normotensive rats using the following procedure:

Female rats (Sprague-Dawley), weighing 175-225 grams, are placed on a diet of sucrose and water overnight. DOCA (deoxycorticosterone acetate), is prepared as a 2.5% suspension in 0.2% hydroxypropyl methyl cellulose. Each rat is administered 0.2 ml. subcutaneously of the DOCA suspension two hours prior to treatment with the test compound.

The suspension or solutions of test compounds are prepared daily. The compounds are suspended in 0.2% hydroxypropyl methylcellulose (vehicle) and administered orally (by gavage) in 2 ml/kg of the rat's body weight. Immediately after dosing, each rat is loaded with an isotonic mixture of NaCl and KCl in the ratio of 40:60 equivalent to 3% of the rat's body weight.

The rats are placed in individual stainless steel metabolism cages. No food or waer is allowed during the experiment. Urine is collected for a four hour period. The volume of urine is measured at four hours and an aliquot is taken for analysis of urine sodium and potassium concentrations. Sodium and potassium are measured using an Instrumentation Labs Digital Flame Photometer. The data are reported in: volume-ml.; sodium and potassium-meq/l.

Standard screening procedures involving the testing of two doses of each compound using 2 rats per dose in a 2-stage screening system. The normal screening doses are 30 and 100 mg/kg orally. Urinary excretions of sodium and potassium are expressed as meq/kg of the rat's body weight.

The data for compounds of Formula I is summarized in the following Table I.

TABLE I

| Compound | Z | $ED_2$ |
|---|---|---|
| 1 | H | 27.3 |
| 2 | 2-F | 40 |
| 3 | 3-F | 63 |
| 4 | 4-F | 7.3 |
| 5 | 2-methyl | 14.3 |
| 6 | 2-Cl | 22.5 |
| 7 | 4-OH | 190 |
| 8 | 2-F | 40 |

Note: X is the same and is chloro for compounds 1-7.
Note: X is methyl for compound 8.

The natriuretic potency of the compounds listed in the above table is reported as an $ED_2$. This is the oral dose (mg./kg.) necessary to produce an excretion in the 0-4 hour period before dosing, of 2-milliequivalents of Na+ per kilogram (meq/kg.) in the rat urine.

The compounds of this invention can be combined with other cardiovascular drugs of different but complementary mechanisms, thereby providing, for example, additive diuretic and antihypertensive effects. Other compounds including the thiazide diuretics, potassium sparing diuretics such as triamterene or spironolactone, antihypertensive compounds including β-blockers such as propranolol, nadolol, atenolol or metoprolol, methyldopa, clonidine or reserpine, vasodilators such as hydralazine or prazosin can be added.

The preferred dosage range for the compounds of this invention is 20 to 100 mg. total dosage daily in a single or divided dose. While the choice of and the amount of the agent to be combined with the compounds of this invention depends on the presence of contraindications and side effects as well as efficacy, suggested amounts of the compounds to be added are as follows: propanolol—80 to 240 mg. per day in divided doses; methyldopa—500 to 1,000 mg. daily in divided doses; clonidine—0.8 to 2.4 mg. daily in divided doses; reserpine—1.0 mg. daily in divided doses; hydralazine—50 to 300 mg. daily in divided doses; and prazosin—4 to 40 mg. daily in divided doses.

While these amounts are preferably added to the preferred dosage range of the compounds of this invention, the choice of agent and the response to therapy may require use of a broader dosage range of the disclosed compounds, namely up to 1 gram per day in a single or divided dose.

What is claimed is:

1. A compound of the formula

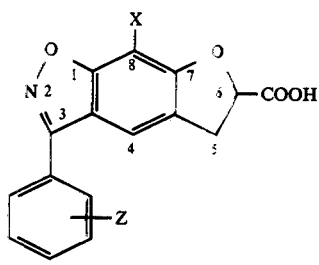

wherein X is hydrogen, loweralkyl, halo, loweralkoxy or trifluoro-methyl, and Z is hydrogen, loweralkyl, halo, hydroxy or alkoxy, or pharmaceutically acceptable salts thereof.

2. A compound of claim 1 of the formula I wherein X is hydrogen, loweralkyl, halo, loweralkoxy or trifluoromethyl, and Z is hydrogen, loweralkyl, halo, hydroxy or loweralkoxy.

3. A compound of claim 2 wherein X is hydrogen, loweralkyl or halo and Z is hydrogen, loweralkyl or halo.

4. A compound of claim 3 wherein X is halo and Z is halo.

5. A compound of claim 3 wherein X is methyl or chloro and Z is methyl, chloro, fluoro or hydroxy.

6. The compound 8-chloro-3-(o-fluorophenyl)-5,6-dihydrofuro-[3,2-f]-1,2-benzisoxazole-6-carboxylic acid.

7. A method of increasing the urinary excretion of a patient comprising administering to a patient in need of such treatment a therapeutically effective amount of a diuretic agent of the formula

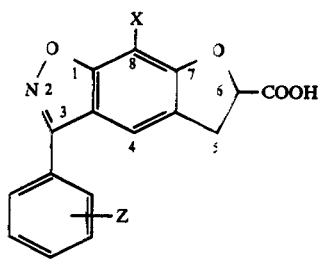

wherein X is hydrogen, loweralkyl, halo, alkoxy or trifluoromethyl, and Z is hydrogen, loweralkyl, halo, hydroxy or alkoxy, or pharmaceutically acceptable salts thereof.

8. A method of claim 7 wherein the diuretic agent is of the formula I wherein X is hydrogen, loweralkyl, halo, alkoxy or trifluoromethyl, and Z is hydrogen, loweralkyl, halo, hydroxy or alkoxy.

9. The method of claim 8 wherein X is hydrogen, loweralkyl or halo and Z is hydrogen, loweralkyl or halo.

10. The method of claim 9 wherein X is halo and Z is halo.

11. The method of claim 10 wherein X is chloro and Z is 2-fluoro.

12. A pharmaceutical composition useful as a diuretic which comprises a compound of the formula

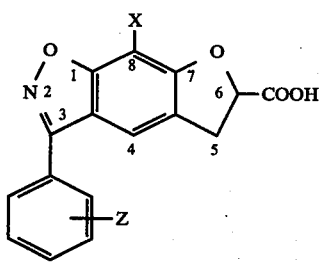

I wherein X is hydrogen, loweralkyl, halo, alkoxy or trifluoromethyl, and Z is hydrogen, loweralkyl, halo, hydroxy or alkoxy, and pharmaceutically acceptable salts thereof, or a pharmaceutically acceptable carrier.

13. A pharmaceutical composition of claim 12 which comprises a compound of the formula

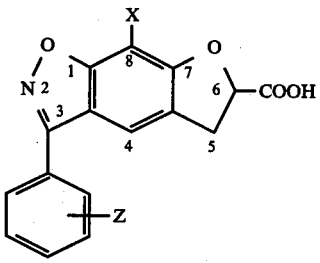

I wherein X is hydrogen, loweralkyl, halo, alkoxy or trifluoromethyl, and Z is hydrogen, loweralkyl, halo, hydroxy or loweralkoxy, and pharmaceutically acceptable salts thereof.

14. The composition of claim 13 wherein X is hydrogen, loweralkyl or halo and Z is hydrogen, loweralkyl or halo.

15. The composition of claim 14 wherein X is halo and Z is halo.

16. The composition of claim 15 wherein X is chloro and Z is 2-fluoro.

* * * * *